US00PP11271P

United States Patent [19]

Kordes

[11] Patent Number: Plant 11,271

[45] Date of Patent: Mar. 7, 2000

[54] HYBRID TEA ROSE PLANT NAMED 'KORLETTE'

[75] Inventor: Wilhelm Kordes, Sparrieshoop, Germany

[73] Assignee: Bear Creek Gardens, Inc., Medford, Oreg.

[21] Appl. No.: 08/985,288

[22] Filed: Dec. 4, 1997

[51] Int. Cl.[7] ..... A01H 5/00

[52] U.S. Cl. ..... Plt./131

[58] Field of Search ..... Plt./12, 11, 13, Plt./130, 131, 132, 139, 138

*Primary Examiner*—Howard J. Locker

*Attorney, Agent, or Firm*—Klarquist Sparkman Campbell Leigh & Whinston, LLP

[57] ABSTRACT

Hybrid tea rose plant having large, novel bi-colored flowers of good petal count and strong fragrance and an angular vigorous growth habit.

1 Drawing Sheet

The present invention relates to a new and distinct variety of rose plant of the hybrid tea class which was originated by me by crossing the variety 'Prima Ballerina' (not patented), with the variety 'Peace,' (U.S. Plant Pat. No. 591).

The primary objective of this breeding was to produce a new rose variety having the fragrance and long pointed buds of the female parent combined with the higher petal count, large flowers, and vigorous growth of the male parent. It was also anticipated some novel colors would come from this cross. The objective was substantially achieved, along with other desirable improvements, as evidenced by the following unique combination of characteristics that are outstanding in the new variety and that distinguish it from its parents, as well as from all other varieties of which I am aware:

1. Very strong fragrance;
2. Novel, bi-color flower color;
3. Vigorous, somewhat angular habit of growth;
4. Petal count intermediate between the parents;
5. Large flower size.

Asexual reproduction of this new variety by budding, as performed at Sparrieshoop, Germany and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Prima Ballerina (unpatented).

*Pollen parent.*—Peace (U.S. Plant Pat. No. 591).

Classification:

*Botanical.*—*Rosa hybrida.*

*Commercial.*—Hybrid Tea.

Flower

Observations made from specimens grown in a garden environment at Sparrieshoop, Germany and Somis, Calif. from January, 1996–August 1997.

Blooming habit: Recurrent.

Bud:

*Size.*—One and one-half inches long when the petals start to unfurl.

*Form.*—The bud form is long, pointed ovoid.

*Color.*—When sepals first divide, bud color is White Group 155D with petal tips and blotches on the rest of the guard petal surface exposed to the sun being Red Group 45C. When half blown, the upper sides of the petals are Red Group 45C fading to Red Group 45D with the lower ¼ to ⅓ of the petal being White Group 155D; and the lower sides of the petals are White Group 155D with a faint blush of Red Group 45D.

*Sepals.*—Color: Green Group 138C but when exposed to sunlight, quite bronzy, close to Greyed-Orange Group 176B. Surface texture: Covered in fine hairs. There are three normally to occasionally heavily appendaged sepals. There are two unappendaged sepals with hairy edges.

*Receptacle.*—Color: Green Group 137D. Shape: Apple. Size: Large (11/16" long×9/16" wide). Surface: Smooth.

*Peduncle.*—Length: Medium (4"). Surface: Smooth, with some small prickles. Color: Medium green (Yellow-Green 146C) and where exposed to the sun bronzy, close to Greyed-Orange Group 176B. Strength: Stiff, erect.

Bloom:

*Size.*—Large. Average open size is five inches.

*Borne.*—Singly.

*Stems.*—Medium (14–18"), strong.

*Form.*—When first open: High centered. Permanence: Retains its form to the end; all petals curl.

*Petalage.*—Number of petals under normal conditions: 25–30.

*Color.*—The upper sides of the petals are Red Group 45C fading to Red Group 45D with the lower ¼ to ⅓ of the petal White Group 155D. The reverse sides of the petals are White Group 155D. The base of each petal has a small (⅜"×⅜"), greenish-white half moon at the point of attachment. The major color on the upper side is Red Group 45C.

*Variegations.*—Occasional greenish-white streak (Green-White Group 157B to C) on both surfaces of the guard petals.

*Discoloration.*—At the end of the first day: No change. At the end of the third day: No change. By day four or five, there is a general fading to Red Group 45D and by day six or seven to Red Group 55B.

*Fragrance.*—Strong.

Petals:

*Texture.*—Thick, leathery.

*Shape.*—Round to slightly deltoid.

*Form.*—Tips slightly recurved.

*Arrangement.*—Imbricated. Petaloids number from none to five (In ten flowers examined) Petaloids are Red Group 45D in color and average 9 ml long and 5 ml wide.

*Persistence.*—Drop off cleanly.

*Lastingness.*—On the plant: Long (seven to eight days). As a cut flower: Long (eight or nine days).

Reproductive parts:

*Anthers.*—Size: Medium. Quantity: Many. Color: Yellow. Arrangement: Regular around styles.

*Filaments.*—Color: Yellow and reddish brown.

*Pollen.*—Color: Gold yellow.

*Styles.*—Color: Reddish.

*Stigmas.*—Color: Greenish-white.

Plant:

*Form.*—Bush.

*Growth.*—Vigorous; upright; branching; Height after one growing season in Somis, Calif. is four and one-half to five feet with the width three and one-half to four feet.

Foliage: Number of leaflets on normal mid-stem leaves: Five or rarely seven.

*Size.*—Large. (6"×5").

*Quantity.*—Normal.

*Color.*—New foliage: Upper and lower surfaces: Greyed-Red Group 178A. Old foliage: Upper surface: Green Group 139A. Lower surface: Green Group 139C.

*Shape.*—Pointed oval.

*Texture.*—Upper side: Leathery.

*Edge.*—Serrated.

*Serration.*—Single, small.

*Petiole rachis.*—Color: Green.

*Petiole underside.*—Smooth with several small prickles and glands.

*Stipules.*—Long (⅝"); serrated, bearded.

*Disease resistance.*—Resistant to mildew and rust under normal growing conditions at Sparrieshoop, Germany and Somis, Calif.

Wood:

*New wood.*—Color: Greyed-Red Group 178A. Bark: Smooth.

*Old wood.*—Color: Group 137C. Bark: Smooth.

Prickles:

*Quantity.*—On main canes from base: Ordinary. On laterals from main canes: Ordinary.

*Form.*—Medium (¼" to ⅜"); hooked downward.

*Color when young.*—Greyed-Red Group 178A.

*Color when mature.*—Yellow-Green Group 146D, changing as the plant ages to Greyed-Orange Group 165C.

Small prickles:

*Quantity.*—On main stalks: None. On laterals: None.

I claim:

1. A new and distinct variety of rose plant of the hybrid tea class, substantially as herein shown and described, characterized particularly as to novelty by novel bi-colored flowers, very strong fragrance, large flower size and good petal count, and upright and angular vigorous growth habit.

* * * * *

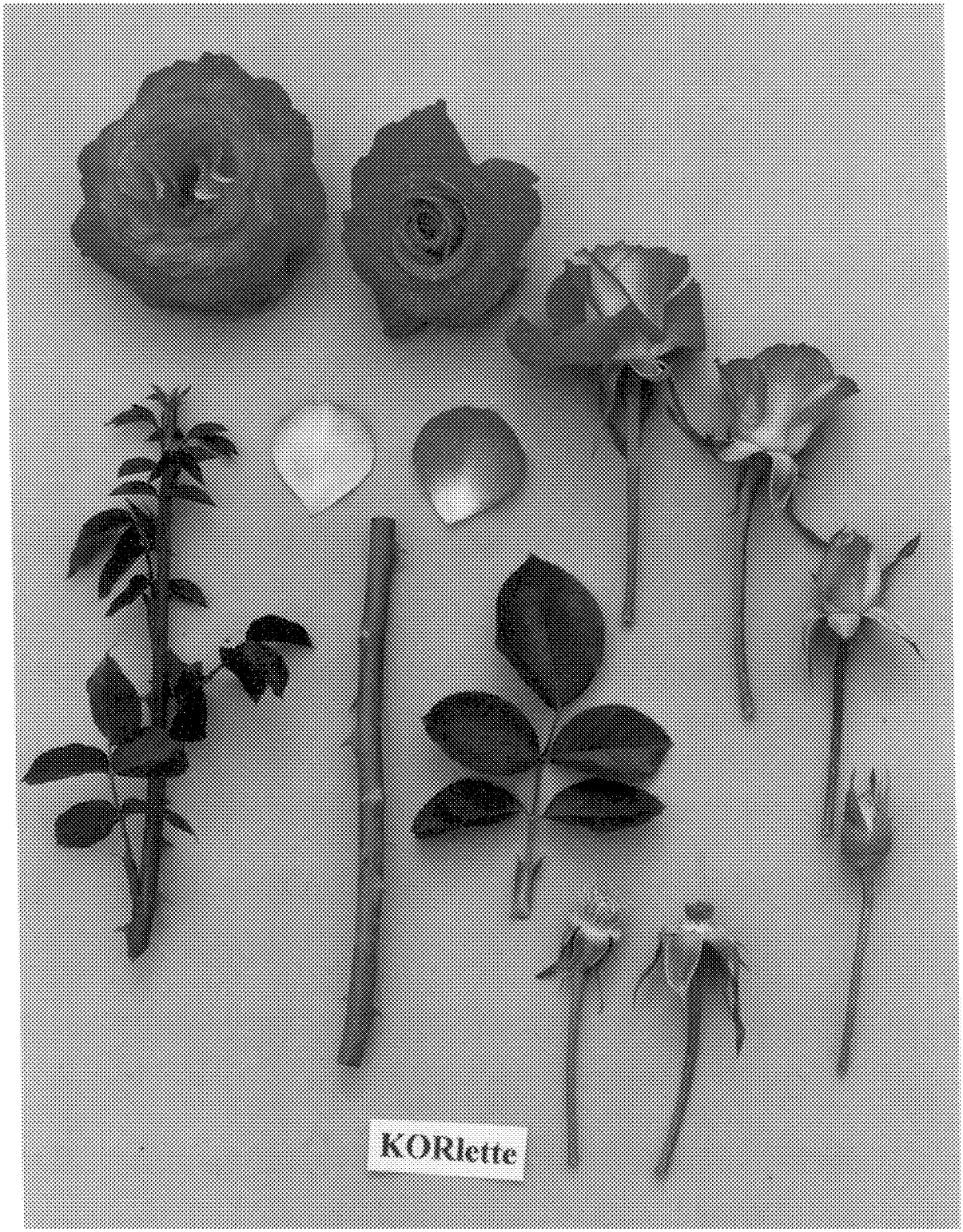
KORlette